(12) United States Patent
Gilbert et al.

(10) Patent No.: US 6,407,107 B1
(45) Date of Patent: Jun. 18, 2002

(54) DERIVATIVES OF BUTYRIC ACID AND USES THEREOF

(75) Inventors: Kathleen Gilbert, Little Rock; E. Kim Fifer, North Little Rock, both of AR (US)

(73) Assignee: The Board of Trustees of the Unversity of Arkansas, Little Rock, AR (US)

( * ) Notice: Subject to any disclaimer, the term of this patent is extended or adjusted under 35 U.S.C. 154(b) by 0 days.

(21) Appl. No.: 09/579,602

(22) Filed: May 26, 2000

Related U.S. Application Data

(60) Provisional application No. 60/136,579, filed on May 28, 1999, now abandoned.

(51) Int. Cl.[7] .................... A61K 31/5375; A61P 43/00; C07D 295/15
(52) U.S. Cl. ..................... 514/237.8; 544/168
(58) Field of Search ........................ 544/168; 514/237.8

(56) References Cited

U.S. PATENT DOCUMENTS 3,234,153 A * 2/1966 Britain

OTHER PUBLICATIONS

Kotelko et al, *Chemical Abstracts*, vol. 79, No. 105, 217, 1973.*
JP 51,023,537 A (Adeka Argus Chem Co Ltd.) Feb. 25, 1976, col. 2, compound #22 . 220.

* cited by examiner

*Primary Examiner*—Robert W. Ramsuer
(74) *Attorney, Agent, or Firm*—Benjamin Aaron Adler

(57) ABSTRACT

The present invention provides a series of compounds having structural formulas

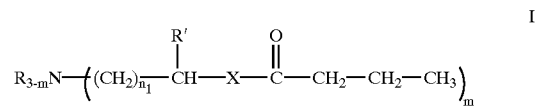

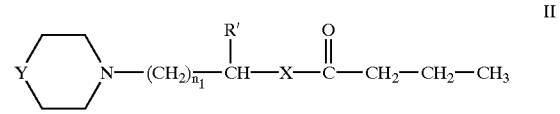

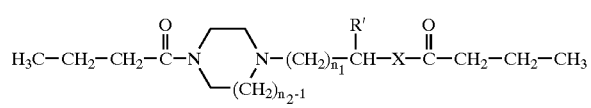

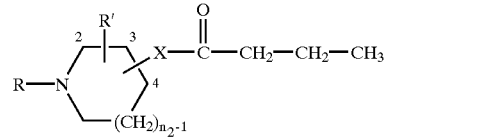

wherein $n_1$ is 1 to 5, $n_2$ is 1 to 4 and m is 1 to 3; X is O or NH; Y is CH2, O, S, NH, NR; R is selected from the group consisting a straight-chain aliphatic group, a branched-chain aliphatic group and an alicyclic group; wherein R' is selected from the group consisting of hydrogen, methyl and ethyl; when Y is O, $n_1$ is not 1; and wherein X and R' are independently optionally substituted at C2, C3 or C4 in compounds of Fomula IV or a pharmaceutically acceptable salt thereof. Also provided is a method of inactivating antigen-specific T cells in an individual.

2 Claims, 12 Drawing Sheets

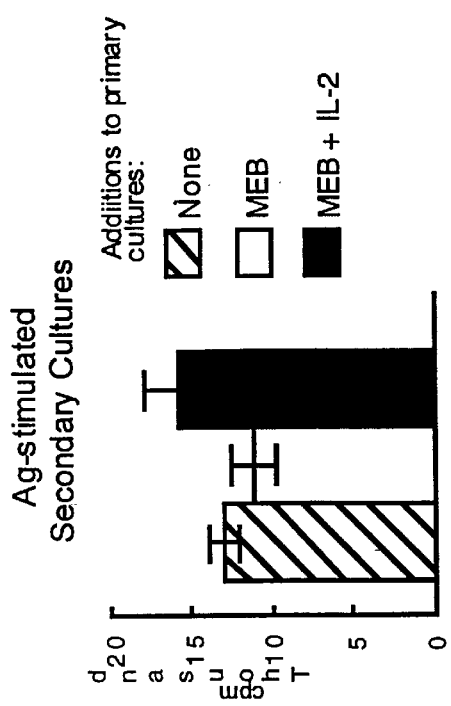
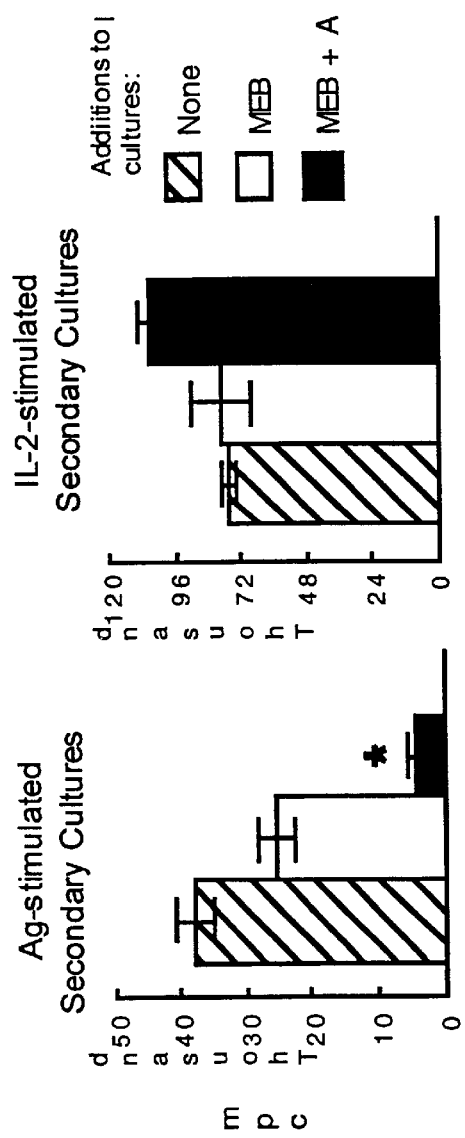
Fig. 5A
Fig. 5B

DERIVATIVES OF BUTYRIC ACID AND USES THEREOF

CROSS-REFERENCE TO RELATED APPLICATION

This application claims the benefit of priority of U.S. provisional patent application Ser. No. 60/136,579, filed May 28, 1999, now abandoned.

BACKGROUND OF THE INVENTION

1. Field of the Invention

The present invention relates generally to the fields of organic chemistry and immunology. More specifically, the present invention relates to derivatives of butyric acid and their use a s inactivators of antigen-specific T cells.

2. Description of the Related Art

Helper T cells (Th) are regulatory lymphocytes which cooperate with other lymphocytes to expedite an immune response. Generally, helper T cells recognize protein antigens after the antigens have been processed into peptide fragments and have become associated with a class II MHC molecules. Autoimmunity is an immune response directed against self-antigens resulting from the breakdown of the normal mechanisms of self-tolerance that prevent the production of functional self-reactive clones of T cells.

Butyric acid is a naturally occurring four carbon fatty acid found in the gut as a result of fiber fermentation. n-Butyrate is well known as an anti-neoplastic agent and for its ability to induce G1 arrest in virtually all cell types tested and to induce cytodifferentiation of many different transformed cell lines. In murine CD4+T cells of the T helper type 1 (Th1), anergy is induced when the cells are pretreated with n-butyrate and antigen thereby becoming unresponsive; i.e., they exhibit a long lasting inability to proliferate or secrete cytokines, to a subsequent stimulation with antigen in secondary cultures (Gilbert & Weigle, J. of *Immunology* 151(3) 1245–1254 (1993)). In contrast, Th1 cells treated with n-butyrate alone, in the absence of antigen stimulation, are totally unaffected by the drug.

Th1 cells exposed to n-butyrate in the presence of antigen lose their ability to proliferate to antigen, but retain their ability to proliferate in cultures stimulated with exogenous Interleukin-2 (IL-2). Therefore, Th1 cell unresponsiveness after exposure to n-butyrate is not caused merely by drug toxicity. Similarly, the inhibitory effects of n-butyrate are not caused by a drug-induced shift in Th1 cell proliferation kinetics. The induction of tolerance with n-butyrate is antigen-dependent, and is linked to a decrease in antigen-induced secretion of IL-2.

The immunotherapeutic potential for n-buytyrate is limited by its short half-life in vivo (3–6 minutes) (Daniel et al., 1989). Even when it is administered by intravenous infusion, n-butyrate is found to be clinically ineffective as an anti-cancer agent (Miller et al., 1987; Novogrodsky et al., 1983). As n-butyrate contains sodium and as it has a half-life of six minutes, large doses are required resulting in a high dose of sodium administered to a patient.

n-Butyrate/tributyrin derivatives with ester and amide functional groups undergo hydrolysis in vivo to release butyrate. This leads to a more sustained release of butyric acid and significantly prolongs the duration of action. These butyrate derivatives also contain an ionizable amino group. This not only allows the compound to be converted to water soluble salts (e.g. hydrochloride), but also avoids the necessity of using the sodium salt of butyric acid which could lead to sodium overload. Therefore, when administered briefly during a n autoimmune response, a member of the butyrate/tributyrin family of drugs acts to convert activated self-reactive T cells to an unresponsive state, but has no effect on the majority of resting T cells.

The prior art is deficient in effective means of using butyrate/tributyrin prodrugs to convert activated self-reactive T-cells during an autoimmune response to an unresponsive state without adversely effecting the majority of resting T cells. The present invention fulfills this long-standing need and desire in the art.

SUMMARY OF THE INVENTION

In one embodiment of the present invention, there are provided a series of compounds having structural formulas

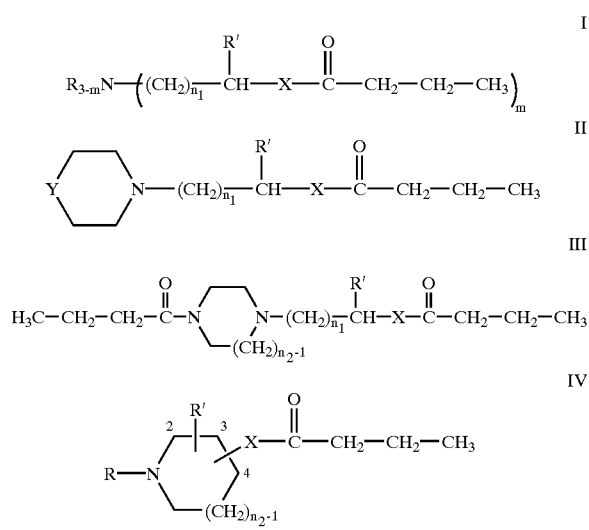

wherein $n_1$ is 1 to 5, $n_2$ is 1 to 4 and m is 1 to 3; X is O or NH; Y is $CH_2$, O, S, NH, NR; wherein R is selected from the group consisting of a straight-chain aliphatic group, a branched-chain aliphatic group and an alicyclic group; wherein R' is selected from the group consisting of hydrogen, methyl and ethyl; wherein when Y is O, $n_1$ can not be 1; and wherein X and R' are independently optionally substituted at C2, C3 or C4 in compounds of Fomula IV or a pharmaceutically acceptable salt thereof.

In another embodiment of the present invention, there is provided a pharmaceutical composition, comprising a compound of the present invention and a pharmaceutically acceptable carrier.

In yet another embodiment of the present invention, there is provided a method of inactivating antigen-specific T cells in an individual in need of such treatment, comprising the step of administering to said individual an effective amount of compound having the structure

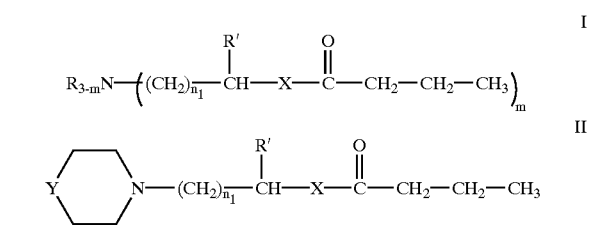

-continued

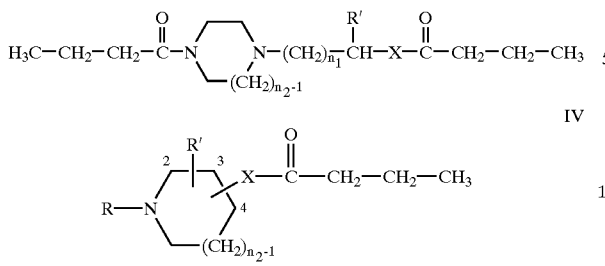

wherein $n_1$ is 1 to 5, $n_2$ is 1 to 4 and m is 1 to 3; X is O or NH; Y is $CH_2$, O, S, NH, NR; wherein R is selected from the group consisting a straight-chain aliphatic group, a branched-chain aliphatic group and an alicyclic group; wherein R' is selected from the group consisting of hydrogen, methyl and ethyl; and wherein X and R' are independently optionally substituted at C2, C3 or C4 in compounds of Fomula IV or a pharmaceutically acceptable salt thereof.

Other and further aspects, features, benefits, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention are briefly summarized. above may be had by reference to certain embodiments thereof which are illustrated in the appended drawings. These drawings form a part of the specification. It is to be noted; however, that the appended drawings illustrate preferred embodiments of the invention and therefore are not to be considered limiting in their scope.

FIG. 2 shows that butyrate derivatives inhibit proliferation of Th1 cells. KLH-specific Th1 cells (clone D3) are stimulated with IL-2 (10% Con A CM) in the presence of different concentrations of n-butyrate or butyrate derivatives.

FIG. 5 shows that MEB induces antigen-specific T cell inactivation in vitro. KLH-specific Th1 cells (clone D3) are incubated in primary cultures with (FIG. 5A) MEB (1 mM) and/or IL-2 (10% Con A CM), or (FIG. 5B) MEB (1 mM) and/or KLH (50 μg/ml). After 2 days, the Th1 cells are isolated from the primary cultures, rested, and then re-incubated in secondary cultures stimulated with antigen (KLH, 50 μg/ml) or IL-2 (10% Con A CM). Th1 cell proliferation in the secondary cultures is measured. *Significantly different from response of Th1 cells exposed to MEB alone, p<0.01.

FIG. 6 shows MEB-induced T cell unresponsiveness is antigen-specific.

DETAILED DESCRIPTION OF THE INVENTION

Figure 1A:
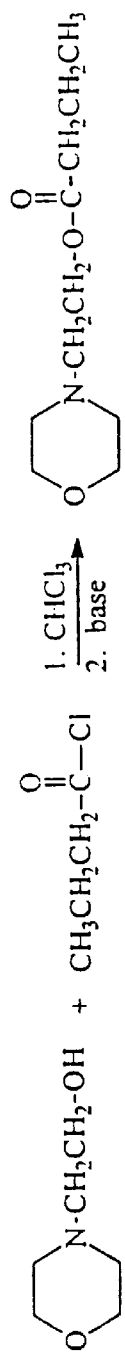
FIG. 1 shows the synthesis of 1 2(4-morpholinyl)ethyl butyrate (FIG. 1A), 2-(4-morpholinyl)ethyl butanamide 2 (FIG. 1B), 2-(4-butanoylpiperazinyl)ethyl butanoate 3 (FIG. 1C), 2,2', 2" (nitrilotrisethyl trisbutyrate 4 (FIG. 1D), and 1-methyl-4-piperidinyl butanoate 5 (FIG. 1E).
Figure 1B:
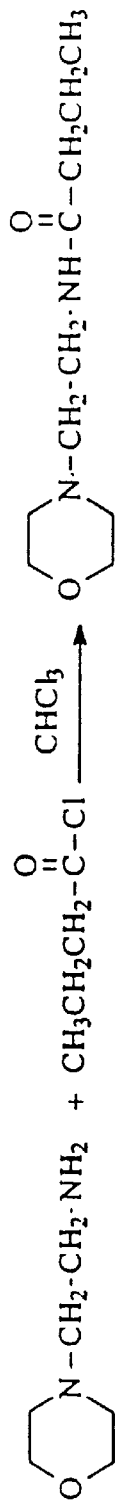
Figure 1C:
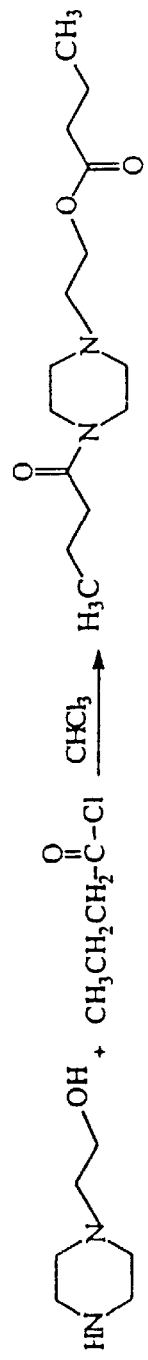
Figure 1D:
Figure 1E:
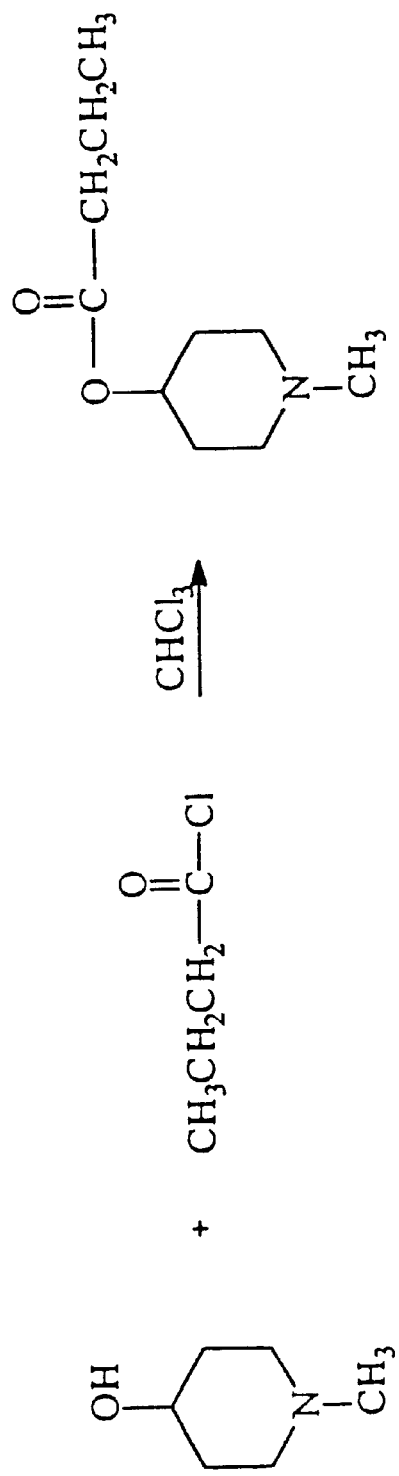

The following abbreviations are used herein: KLH: keyhole limpet hemocyanin; PBS: phosphate buffered saline; Con A CM: conditioned medium from rat spleen cells stimulated with Concanavalin A; IL-2: interleukin-2; IL-4: interleukin-4; APC: antigen presenting cells; MEBA: 2-(4-Morpholinyl)ethyl butanamide hydrochloride; BEB: 2-(4-

Butanoylpiperazinyl)ethyl butanoate hydrochloride; MEB: 2-(4-Morpholinyl)ethyl butyrate hydrochloride.

As used herein, the term "individual" shall refer to animals and humans.

The present invention provides ester, amide and ester/amide derivatives of n-butyric acid. The general structures of the compounds of the present invention and synthetic schemes of said compounds are shown in FIG. 1. These butyrate prodrugs contain an ionizable amino group which, when converted to a water soluble salt, increases the overall aqueous solubility. The ester and/or amide functional groups undergo hydrolysis to release butyric acid. The optional substitution of the carbon adjacent to the X group by a methyl or ethyl provides steric hindrance, thereby slowing the in vivo hydrolysis rate and increasing the half-life of the parent compounds. Thus, this sustained release of butyric acid coupled with a longer half-life maintains a butyrate blood level over a longer period of time and increases the dosing interval.

The butyrate prodrugs and methods of the present invention may be used to inactivate antigen-specific T cells thereby providing immunotherapeutic methods to treat autoimmune diseases, to treat or to prevent other disorders involving an autoimmune component and as anti-cancer reagents. Using butyrate prodrugs is more advantageous than using traditional immunosuppressive drugs. Treatment is short term, rather than long term; the prodrugs of the present invention induce T-cell anergy instead of temporarily suppressing T-cell activity. Additionally, unlike most immunosuppressive drugs, butyrate and its prodrugs are non-toxic.

Autoimmune diseases are characterized by immune cell destruction of self cells, tissues and organs. In systemic autoimmune diseases where lack of information concerning the self-proteins targeted by the auto-reactive T-cells precludes peptide-based immunotherapies, the time-release characteristics of butyrate prodrugs are beneficial. Representative examples of such autoimmune diseases are rheumatoid arthritis diabetes, multiple sclerosis and systemic lupus erythematosus.

The immunotherapeutic method of the present invention is also useful in terms of allograft and xenograft transplantation rejection. Concurrent administration of a butyrate prodrug enhances the tolerogenicity of donor cells, and thereby increases the likelihood of engraftment.

The compounds and methods of the present invention may also be used to treat neoplastic diseases. Previously, the use of n-butyrate as an anti-cancer reagent was thwarted by its rapid excretion rate. The varied rates of hydrolysis of the butyrate prodrugs of the present invention and their longer half-lives provide a more effective means of treatment. Representative examples of such neoplastic diseases which could be treated using these compounds and methods are renal cancer, ovarian cancer, lung cancer, glioma and leukemia.

The methods of the present invention may be used to treat any animal. Most preferably, the methods of the present invention are useful in humans.

Pharmaceutical compositions are prepared using the novel prodrugs of the butyrate/tributyrin family of drugs of the present invention. In such a case, the pharmaceutical or immunogenic composition comprises the novel compounds of the present invention and a pharmaceutically acceptable carrier. A person having ordinary skill in this art would readily be able to determine, without undue experimentation, the appropriate dosages and routes of administration of the novel compounds of the present invention.

Compounds of the present invention, pharmaceutically acceptable salt thereof and pharmaceutical compositions incorporating such, may be conveniently administered by any of the routes conventionally used for drug administration, e.g., orally, topically, parenterally, or by inhalation. The compounds of the present invention may be administered in conventional dosage forms prepared b y combining the compound with standard pharmaceutical carriers according to conventional procedures. The compounds of the present invention may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable carrier or diluent is dictated by the amount of active ingredient with which it is to be combined, the route of administration and other well known variable. The carrier(s) must be "acceptable" in the sense of being compatible with the other ingredients of the formulation and not deleterious to the recipient thereof.

The pharmaceutical carrier employed may be, for example, either a solid or a liquid. Representative solid carriers are lactose, terra alba, sucrose, talc, gelatin, agar, pectin, acacia, magnesium sterate, stearic acid and the like. Representative liquid carriers include syrup, peanut oil, olive oil, water and the like. Similarly, the carrier may include time delay material well known in the art such as glyceryl monosterate or glyceryl disterarate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 gram. When a liquid carrier is used, the preparation will be in the form of a syrup, emulsion, soft gelatin capsule, sterile injectable liquid such as an ampule or nonaqueous liquid suspension.

Compounds of the present invention may be administered topically (non-systemically). This includes the application of a compound externally to the epidermis or the buccal cavity and the instillation of such a compound into the ear, eye and nose, such that the compound does not significantly enter the bloodstream. Formulation suitable for topical administration include liquid or semi-liquid preparations suitable for penetration through the skin to the site of inflammation such as liniments, lotions, creams, ointments, pastes and drops suitable for administration to the ear, eye and nose. The active ingredient may comprise, for topical administration from 0.001% to 10% w/w, for instance from 1% to 2% by weight of the Formulation. It may however, comprise as much as 10% w/w but preferably will comprise less than 5% w/w, more preferably from 0.1% to 1% w/w of the Formulation.

Lotions according to the present invention include those suitable for application to the skin and eye. An eye lotion may comprise a sterile aqueous solution optionally containing a bactericide and may be prepared by methods similar to those for the preparation of drops. Lotions or liniments for application to the skin may include an agent to hasten drying and to cool the skin, such as an alcohol or acetone, and/or a moisterizer such as glycerol or an oil such as castor oil or arachis oil.

Creams, ointments or pastes according to the present invention are semi-solid formulations of the active ingredient for external application. They may be made by mixing the active ingredient in finely divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap, a mucilage, an oil of natural origin such as almond, corn, archis, castor, or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving. Alternatively, the solution may be sterilized by filtration and transferred to the container by an aseptic technique. Examples of bactericidal and fungicidal agents suitable for inclusion in the drops are phenymercuric nitrate or acetate (~0.002%), benzalkonium chloride (~0.01%) and chlorhexidine acetate (~0.01%). Suitable solvents for the preparation of an oily solution include glycerol, diluted alcohol and propylene glycol.

Compounds of the present invention may be administered parenterally, i.e., by intravenous, intramuscular, subcutaneous, intranasal, intrarectal, intravaginal or intraperitoneal administration. The subcutaneous and intramuscular forms of parenteral administration are generally preferred. Appropriate dosage forms for such administration may be prepared by conventional techniques. Compounds may also be administered by inhalation, e.g., intranasal and oral inhalation administration. Appropriate dosage forms for such administration, such as aerosol formulation or a metered dose inhaler may be prepared by conventional techniques well known to those having ordinary skill in this art.

For all methods of use disclosed herein for the compounds of the present invention, the daily oral dosage regiment will preferably be from about 0.1 to about 100 mg/kg of total body weight. The daily parenteral dosage regiment will preferably be from about 0.1 to about 100 mg/kg of total body weight. The daily topical dosage regimen will preferably be from about 0.01 to about 1 g, administered one to four, preferably two to three times daily. It will also be recognized by one of skill in this art that the optimal quantity and spacing of individual dosages of a compound of the present invention, or a pharmaceutically acceptable salt thereof, will be determined by the nature and extent of the condition being treated and that such optimums can be determined by conventional techniques.

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid. In addition, pharmaceutically acceptable salts of compounds of the present invention may also be formed with a pharmaceutically acceptable cation, for instance, if a substituent group comprises a carboxy moiety. Suitable pharmaceutically acceptable cations are well known in the art and include alkaline, alkaline earth ammonium and quaternary ammonium cations.

Thus the present invention is directed toward the effective use of agents to induce T cell anergy. More specifically, this invention uses ester and/or amide derivatives of butyric acid to inactivate antigen-specific T cells thus providing immunotherapeutic methods of treatment of autoimmune diseases, disorders involving an autoimmune component and neoplastic diseases such renal cancer, ovarian cancer, lung cancer, glioma and leukemia, etc.

n-Butyrate derivatives designed to possess GI blocker activity both in vitro and in vivo are synthesized. The ester (MEB) and ester/amide (BEB) derivatives of butyrate are found to suppress IL-2-stimulated proliferation of Th1 cells in vitro. Unlike MEB and BEB, the amide analogue of butyrate, MEBA, does not suppress Th1 cell proliferation in vitro. The lack of activity of MEBA may be related to the slower metabolic hydrolysis of the amide bond in MEBA compared to the ester bond in MEB and BEB. When tested in vivo, both MEB and BEB, but not MEBA, are shown to significantly suppress a primary antibody response to a thymus-dependent antigen. Suppression of antibody production reflects inhibition of T cell function and/or B cell function. However, in vivo examination of the effect of MEB on T cell activity revealed that MEB induced antigen-specific unresponsiveness in $CD4^+T$ cells. The T cell unresponsiveness induced in mice immunized with ovalbumin and treated with MEB is manifested as an inability of lymph node $CD4^+T$ cells to proliferate when stimulated with ovalbumin in vitro. Although this does not negate the possibility that MEB may also inactivate antigen-activated B cells, it clearly demonstrates that ester analogues of butyrate induce unresponsiveness in antigen-specific $CD4^+T$ cells.

The following examples are given for the purpose of illustrating various embodiments of the invention and are not meant to limit the present invention in any fashion.

EXAMPLE 1
Animals

Male C57BL/10, DBA/2 and C3H/HeJ mice at 6 to 8 wk of age were purchased from Harlan Sprague Dawley, Inc (Indianapolis, Ind.).

EXAMPLE 2
Reagents and antibodies

Inject KLH was purchased from Pierce (Rockford, Ill.) and n-butyrate was purchased from Sigma (St. Louis, Mo.). Butyryl chloride, 4-(2-hydroxyethyl)morpholine, 4-(2-aminoethyl)morpholine, and 1-(2-hydroxyethyl)piperazine were purchased from Aldrich (Milwaukee, Wis.).

EXAMPLE 3
Instrumentation

Proton NMR spectra were recorded at 500 MHz on a Bruker AM500 spectrometer and chemical shifts are reported in p.p.m. Mass spectra were recorded on a Finnegan TSQ 700 spectrometer (direct exposure probe) at 70 eV electron ionization.

EXAMPLE 4
Synthetic schema of butyrate derivatives 1-(4-Morpholinyl) ethyl butyrate (MEB) 1

Butyryl chloride (6.07 g, 0.06 mol) was added with stirring to a cooled solution of 5 g (0.04 mol) of 4-(2-hydroxyethyl)morpholine in 20 ml of chloroform over 45 min and cooling was maintained for 6 h. The mixture was diluted with chloroform (15 ml) and washed three times with 20 ml of 5% sodium carbonate. The aqueous layer was washed with 15 ml of chloroform, and the combined organic layers were dried over anhydrous sodium sulfate, filtered, and concentrated in vacuo to afford 5.37 g (70%) of the ester as an orange liquid. Column chromatography of 500 mg on silica gel 60 (0.063–0.200 mm, 10 inch, 30 mm inside diameter) was performed using a gradient of ethyl acetate/hexane 1:3 to ethyl acetate. The recovered sample afforded the following: $^1$H NMR (CDCl$_3$)$_{13}$ 0.93 (t, 3H, J=7.4, CH$_3$), 1.63 (m, 2H, J=7.4, CH$_3$CH$_2$—), 2.28 (t, 2H, J=7.4, COCH$_2$—), 2.58 (ap bs, 4H, ring N—CH$_2$—), 2.69 (t, 2H, J=5.7, CO$_2$CH$_2$—), 3.74 (t, 4H, J=4.5, ring —OCH$_2$—), 4.25 (t, 2H, J=5.7, NCH$_2$—); MS m/z 201 (M$^+$), 130, 113, 100 (Base Peak).

1-(4-Morpholinyl)ethyl butyrate hydrochloride

A solution of 2.5 g of the crude free base in 60 ml of anhydrous ether was cooled in an ice bath with stirring while 14 ml of a cold 1.0 M solution of hydrogen chloride in anhydrous ether was added dropwise. The resulting white solid was filtered and recrystallized from 60 ml of tetrahydrofuran to yield 1.69 g of white crystals: mp 108.0–108.3° C.

2-(4-Morpholinyl)ethyl butanamide (MEBA) 2

The amide was synthesized in 68% yield in a manner analogous to that described for MEB by treatment of 4-(2-aminoethyl)morpholine with butyryl chloride. $^1$H NMR (CDCl$_3$)$_{13}$ 0.91 (t, 3H, J=7.4, CH$_3$), 1.62 (m, 2H, CH$_3$CH$_2$—), 2.13 (t, 2H, J=7.4, COCH$_2$—), 2.40–2.45 (m, 6H, N—CH$_2$— & ring O—CH$_2$—), 3.30–3.33 (m, 2H, N—CH$_2$—), 3.66 (t, 4H, ring N—CH$_2$—), 5.96 (bs, 1H, NH); MS m/z 200 (M$^+$), 182, 157, 113, 100 (Base Peak).

2-(4-Morpholinyl)ethyl butanamide hydrochloride

The hydrochloride salt was prepared as described for MEB and recrystallized from tetrahydrofuran to afford hygroscopic crystals: mp 150.6–151.1° C.

Synthesis of 2-(4-Butanoylpiperazinyl)ethyl butanoate (BEB) 3

Butyryl chloride (11.83 g, 0.11 mol) was added dropwise to a cooled solution of 4.84 g (0.04 mol) of 1-(2-hydroxyethyl)-piperazine in 20 ml of chloroform. Cooling was maintained for 2 h, and a white precipitate formed. Chloroform (15 ml) was added and the mixture was stirred overnight, washed with 210 ml of cold 0.6 N sodium hydroxide solution, then washed twice with 50 ml of cold water. The organic fraction was dried over anhydrous sodium sulfate, filtered and, concentrated in vacuo to yield 9.39 g (94%) of a clear yellow liquid. This was distilled: bp 144–146° C., (0.5 mm Hg) to give 6.08 g (65%) of MEB. $^1$HNMR (CDCl$_3$) δ 0.897 (t, 3H, J=7.4, CH$_3$), 0.901 (t, 3H, J=7.4, CH$_3$), 1.59 (m, 2H, CH$_3$CH$_2$), 1.61 (m, 2H, CH$_3$CH$_2$), 2.24 (t, 2H, J=7.4, CH$_2$CO), 2.25 (t, 2H, J=7.4, CH$_2$CO), 2.42–2.43 (app t, 2H, J=5.2, axial CH ester end of ring), 2.43–2.44 (app t, 2H, J=5.2, equatorial CH ester end of ring), 2.59 (t, 2H, J=5.8, N—CH$_2$—CH$_2$—O), 3.41 (app t, 2H, axial CH amide end of ring), 3.57 (app t, 2H, equatorial CH amide end of ring), 4.16 (t, 2H, N—CH$_2$—CH$_2$—O); MS m/z 270 (M$^+$), 255, 242, 227, 199, 182, 169 (Base Peak).

2-(4-Butanoylpiperazinyl)ethyl butanoate hydrochloride

The hydrochloride salt was prepared as described for MEB and recrystallized twice from tetrahydrofuran to afford white crystals: mp 130.1–130.7° C.

Synthesis of 2,2', 2"-Nitrilotrisethyl trisbutyrate (4)

Butyryl chloride 12.01 g. (0.11 mol) was added dropwise with stirring to a cooled solution of 3 g (0.02 mol of triethanolamine in 20 ml of chloroform. Stirring was continued for 48 h. The reaction mixture was washed three times with 40 mL of 5% sodium carbonate. The aqueous layer was washed with 15 ml of chloroform and the combined organic layers were dried over anhydrous sodium sulfate, filtered, and concentrated in vacuo to yield 6.77 g (94% of a pale yellow liquid. After conversion to the hydrochloride and back to the free base the following spectral data were obtained: $^1$H NMR (CDCl$_3$) δ 0.90 (t, 9H, J=7.4, CH$_3$), 1.60 (m, 6H, J=7.4, CH$_3$CH$_2$CH$_2$), 2.23 (t, 6H, J=7.4, CH$_2$COO), 2.81 (t, 6H, J=7.4, CH$_2$N), 4.09 (t, 6H, J=7.4, OCH$_2$); MS m/z 359 (m$^+$), 344, 316, 288, 258, 115 (base).

2,2', 2"-Nitrilotrisethyl trisbutyrate hydrochloride

The hydrochoride salt was prepared as described for MEB, but it was very hygroscopic and readily oiled out. Attempts to recrystallize it were unsuccessful.

1-Methyl-4-piperidinyl butanoate (5)

The butanoate ester of 4-hydroxy-1-methylpiperidine was synthesized by a method similar to that described for MEB by treatment of 4-hydroxy-1-methylpiperidine with butyryl chloride to afford a yellow oil (97% yield). Distillation (bp 46–50°, 0.5 mm Hg) gave a colorless liquid (92%). $^1$H NMR (CDCl$_3$) δ 0.92 (t, 3H, CH$_2$CH$_3$), 1.58–1.66 (m, 2H, J=7.4, CH$_2$CH$_3$), 1.66–1.71 (m, 2H, ring C-3 & C5 ax H), 1.85–1.89 (m, 2H, ring C-3 & C5 eq H), 2.18–2.26 (app t, 2H, ring C2 & C6 ax H), 2.24 (t, 2H, CH$_2$COO), 2.24 (s, 3H, NH), 2.61 (app br s, 2H ring C2 & C6 eq H), 4.76 (m, 1H, ring C-4 ax H). MS m/z 185 (m$^+$), 114, 98, 97, 96 (base), 82, 70, 57, 55.

1-Methyl-4-piperidinyl butanoate hydrochloride

The hydrochloride salt was prepared as described for MEB and was recrystallized from tetrahydrofuran to give white crystals: m.p. 132.2–133.70° C.

EXAMPLE 5

Th1 cell clones

The KLH-specific were developed in C57BL/10 mice, and characterized as Th1 clones based on their ability to secrete IL-2, but not IL-4. The Th1 clones were passed every 7–14 days using KLM, irradiated syngeneic spleen cells as antigen-presenting cells (APC), and IL-2-containing Con A CM using a previously described protocol (Gilbert et al., 1990).

EXAMPLE 6

Suppressive Effects of Butyrate Prodrugs in vitro and in vivo

Prior to testing the suppressive effects of butyrate prodrugs in vivo, the ability of n-butyrate to inhibit a primary antibody response in mice was examined. As shown in Table 1 below, n-butyrate itself did not suppress a primary antibody response by more than 40–50%.

TABLE 1

| Anti-HGG antibody in serum of individual mice | | | |
|---|---|---|---|
| Experiment 1 | | Experiment 2 | |
| Control | n-Butyrate treated | Control | n-Butyrate treated |
| 56 | 29 | 15 | 4 |
| 270 | 83 | 6 | 9 |
| 118 | 24 | 13 | 31 |

TABLE 1-continued

Anti-HGG antibody in serum of individual mice

| Experiment 1 | | Experiment 2 | |
|---|---|---|---|
| Control | n-Butyrate treated | Control | n-Butyrate treated |
| 126 | 202 | 40 | 12 |
| 183 | 91 | 39 | 6 |
| x=150±80 | x = 86 ± 72 | x = 23 ± 16 | x = 12 ± 11 |

Aggregated human gammaglobulin (HGG) was injected (100 μg) into mice ip on day 0, followed by ip injections of 5.5 mg n-butyrate on days 2–5 (Experiment 1) or 2–6 (Experiment 2). Levels of anti-HGG antibody were measured by ELISA on day 9.

EXAMPLE 7

Butyrate derivatives reversibly inhibited IL-2-induced proliferation of Th1 cells To test the ability of the butyrate derivatives to suppress T cell activity in vivo, Th1 cells [($5\times10^4$ cells/well in 96 well plates (Costar)] are stimulated with 10% IL-2-containing Con A CM in the presence of various concentrations of different butyrate derivatives. In some cultures, Th1 cell proliferation is measured after two days. In other cultures, the Th1 cells are washed after 24 hours, and fresh IL-2-containing medium is added. Proliferation is measured in the washed, IL-2-restimulated cultures after an additional 2 days.

Figures 2A, 2B:
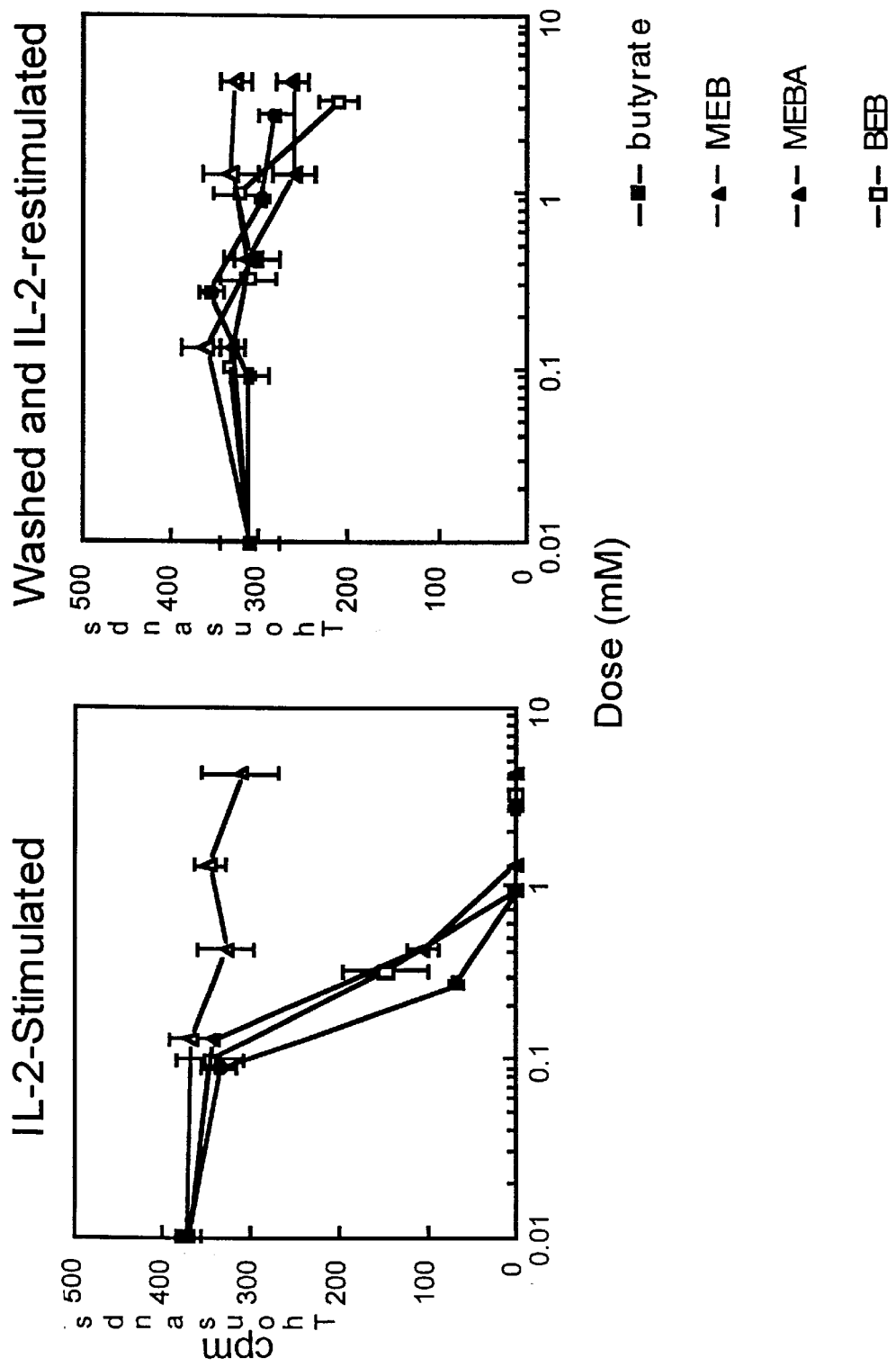
In FIG. 2A Th1 cell proliferation is measured after 2 days.
In FIG. 2B, the inhibitors are washed out after 24 hours, and the Th1 cells reincubated with fresh IL-2-containing medium. Proliferation of the Th1 cells restimulated with IL-2 in the absence of the inhibitors is measured after an additional 2 days. This experiment was repeated three times, and the proliferation data represents the means of the four experiments.

As shown in FIG. 2, the ester and ester/amide derivatives of n-butyrate, MEB and BEB respectively, are comparable to n-butyrate in their ability suppress IL-2-induced proliferation of Th1 cells. In addition, similar to n-butyrate-treated T cells, T cells treated with butyrate derivatives regained their ability to proliferate to IL-2 once the compounds are washed out of the cultures. This later observation means that the cell cycle blocking effects of the MEB and BEB are not due to drug-induced toxicity.

EXAMPLE 8

Butyrate derivatives inhibited antibody production to thymus-dependent antigen in vivo The butyrate derivatives are tested for their ability to suppress lymphocyte activity in vivo. C57BL/10 mice (5 mice/group) are injected ip with 100 μg of ovalbumin in conjunction with complete Freund's adjuvant on Day 0. In one experiment, the mice also receive one ip injection per day of the butyrate derivatives (0.091 mmol) on Days 1–3. Serum samples are obtained 10 days after the initial injection with ovalbumin, and tested for the presence of anti-ovalbumin antibodies using an ELISA. To perform the ELISA 96 well plates (Costar 3595) are first incubated with ovalbumin (100 μl/well of 100 μg/ml in PBS) overnight at 4° C. The plates are then washed 4 times with PBS and 0.5% Tween 20, blocked with 1% fetal calf serum for 30 minutes at 37° C., and washed again. Individual serum samples are added (diluted 1/100 or 1/1000 in PBS), and the plates are incubated for 2 hours at 20° C. The plates were next washed 7 times with PBS/Tween, and alkaline phosphate (AP)-labeled goat anti-mouse IgG, IgA, IgM (H+L) (Zymed) is added (1/1000) for 1 hour at 20° C. The plates are again washed 7 times with PBS/Tween, alkaline phosphate substrate (1 mg/ml) is added. After 10 minutes, Ig levels are quantified by an ELISA reader (absorbance 405 nm). The concentration of anti-ovalbumin is determined by comparison with a standard curve obtained using mouse anti-ovalbumin antibody (Sigma; St. Louis, Mo.). To measure isotype-specific anti-ovalbumin antibodies, serum samples (diluted at 1/300 or 1/1000) are incubated on the ovalbumin-coated plates as described above. After washing, biotinylated detecting antibodies directed against mouse $IgG_{2a}$ (rat $IgG_1$, clone R19-15), $IgG_{2b}$ (rat $IgG_{2a}$, clone R12-3) $IgG_1$ (rat $IgG_1$, clone A85-1), or IgM (rat $IgG_{2a}$, clone R6-60.2) (all purchased from PharMingen, La Jolla, Calif.) areadded at 2.5 μg/ml for one hour at 20° C. followed by AP-labeled ExtrAvidin (Sigma) for one hour at 20° C. and AP substrate. Ig levels are presented as OD measurements.

Figure 3:
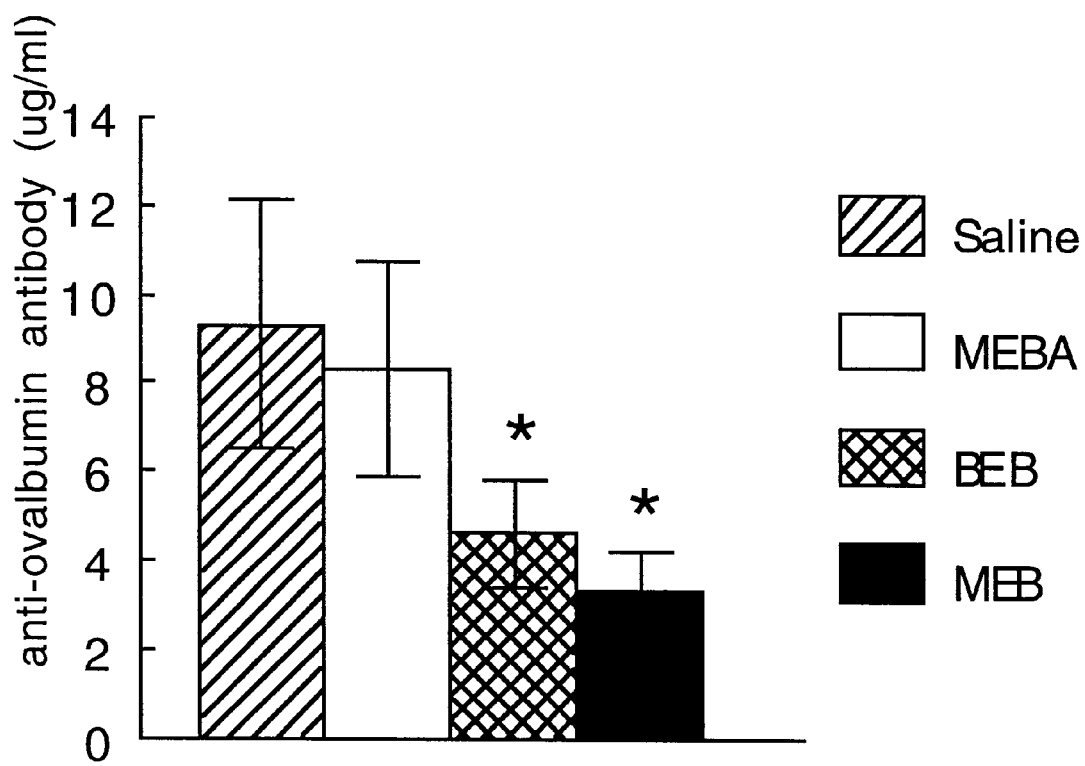
FIG. 3 shows that MEB inhibits primary antigen-specific antibody production in vivo. C57BL/10 mice are injected ip on Day 0 with ovalbumin followed by ip injections of saline, or one of three different butyrate derivatives on Days 1–3. Levels of total anti-ovalbumin antibody in the serum 10 days following antigen administration are measured. *Significantly different from response of mice treated with saline, p<0.05.

When anti-ovalbumin levels in the serum of the mice are tested 10 days following administration of the antigen, MEB is shown to significantly decrease by 65% the ability of the mice to generate a primary antibody response to a thymus-dependent antigen as compared to control mice treated with saline (FIG. 3). Mice treated with a second butyrate derivative, BEB, also produced significantly less antigen-specific antibody than control mice. In contrast, the third butyrate derivative, MEBA, is unable to suppress antigen-specific antibody production in vivo. These results show that the ester and the ester/amide derivatives of butyrate suppressed lymphocyte function both in vitro and in vivo, while the amide analogue of butyrate was ineffective both in vitro and in vivo.

EXAMPLE 9

Butyrate derivatives inhibited antigen-specific T cell responses in vivo

If the butyrate derivatives suppressed antibody production to a thymus-dependent antigen by inactivating the antigen-specific $CD4^+T$ cells required for B cell help, then the butyrate derivatives need only be present during an early stage during which the $CD4^+T$ cells would otherwise be activated by antigen. To demonstrate that short term exposure to butyrate derivatives alters the T cell response to antigen in vivo, male C57BL/10 mice (5 per group) are injected ip with 100 μg of ovalbumin in conjunction with complete Freund's adjuvant on Day 0, followed by a single ip injection of saline or MEB (0.15 mmol) on Day 2 or 3. On day 10 the mice receive 100 μg ovalbumin in conjunction with incomplete Freund's adjuvant sc at the base if the tail. After an additional 7 days, cells from the periaortic and mesenteric lymph nodes were enriched for $CD4^+T$ cells by negative selection (Griffin et al., 1998). The T cells are then incubated at $1\times10^5$ in half-area (100 μl/well) 96 well plates (Costar 3696) along with $2\times10^5$ irradiated (2000R) spleen cells from untreated C57BL/10 mice as APC, and various concentrations of ovalbumin. Proliferation is measured on day 4 by assessing incorporation of [$^3$H]-TdR after a 12 hour pulse.

Figure 4A:
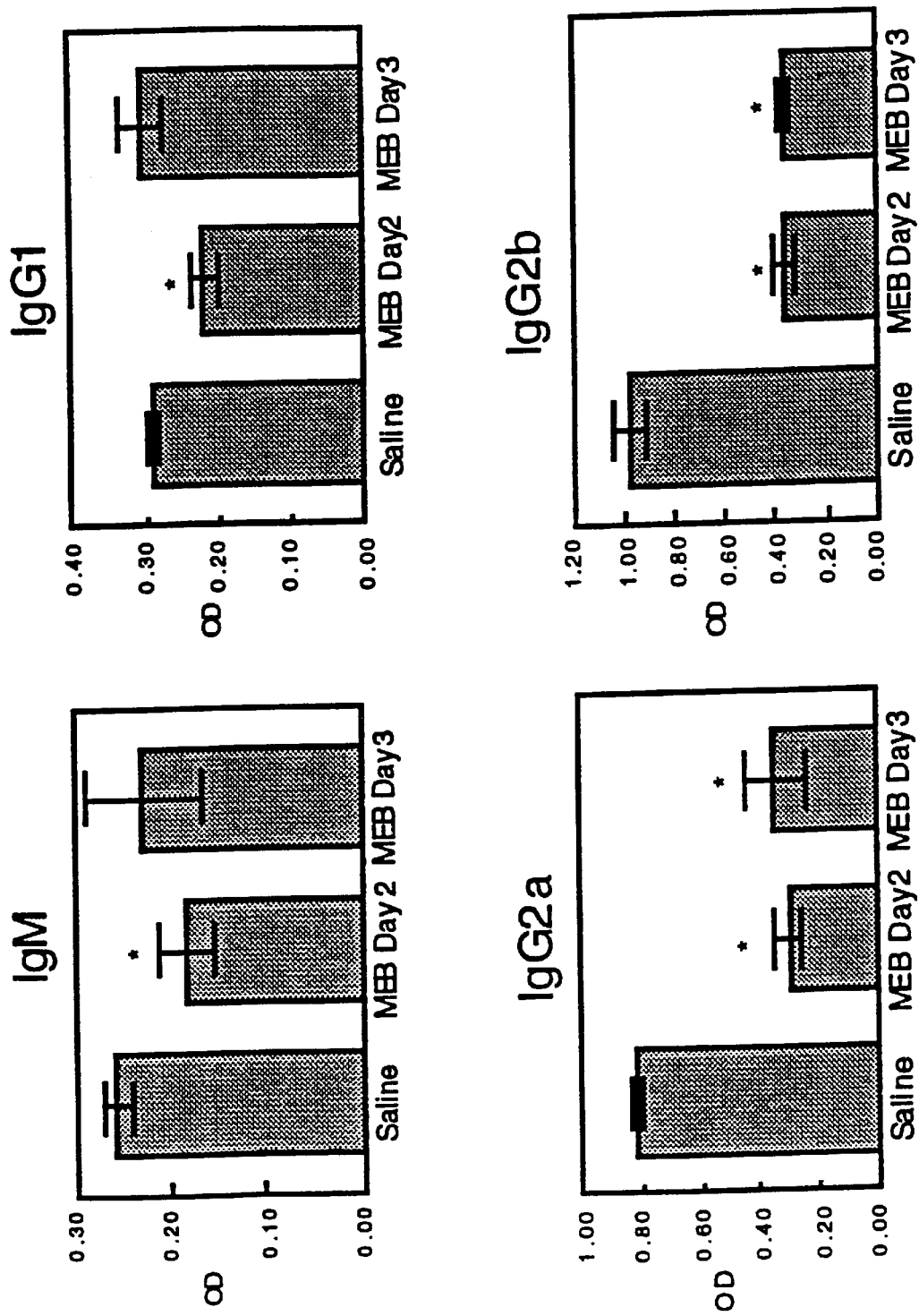
FIG. 4 shows that MEB induces antigen-specific T cell inactivation in vivo. C57BL/10 mice are injected ip with ovalbumin/CFA on day 0, followed by a single ip injection of saline or MEB (0.15 mmol) on Days 2 or 3. The mice are reimmunized with ovalbumin sc on Day 10. Isotype-specific anti-ovalbumin antibody generated during the primary immune response (FIG. 4A), and the secondary immune response (FIG. 4B) are measured in the serum at day 10 and day 16, respectively.
(FIG. 4C). Lymph node $CD4^+T$ cells isolated from the mice 6 days after the second immunization with ovalbumin are stimulated with ovalbumin in vitro, and examined for proliferation. *Significantly different from response $CD4^+T$ cells isolated from mice treated with saline, p<0.05. This experiment was repeated, and the proliferation data represents the means of the two experiments.

Isotype-specific anti-ovalbumin antibody is measured to more precisely delineate the effect of MEB on antigen-specific antibody production. In addition, to look more directly on the effect of MEB on $CD4^+T$ cells, lymph node $CD4^+T$ cells isolated from mice 6 days after the second immunization with ovalbumin are examined for their ability to proliferate to ovalbumin in vitro. Treatment with a single dose of MEB significantly decreased the production of $IgG_{2a}$ and $IgG_{2b}$ anti-ovalbumin antibody during the primary antibody response (FIG. 4A). $IgG_1$ and IgM anti-ovalbumin antibody production is also decreased, albeit not dramatically, if MEB is administered on day 2, but not on day 3, following immunization.

Figure 4B:
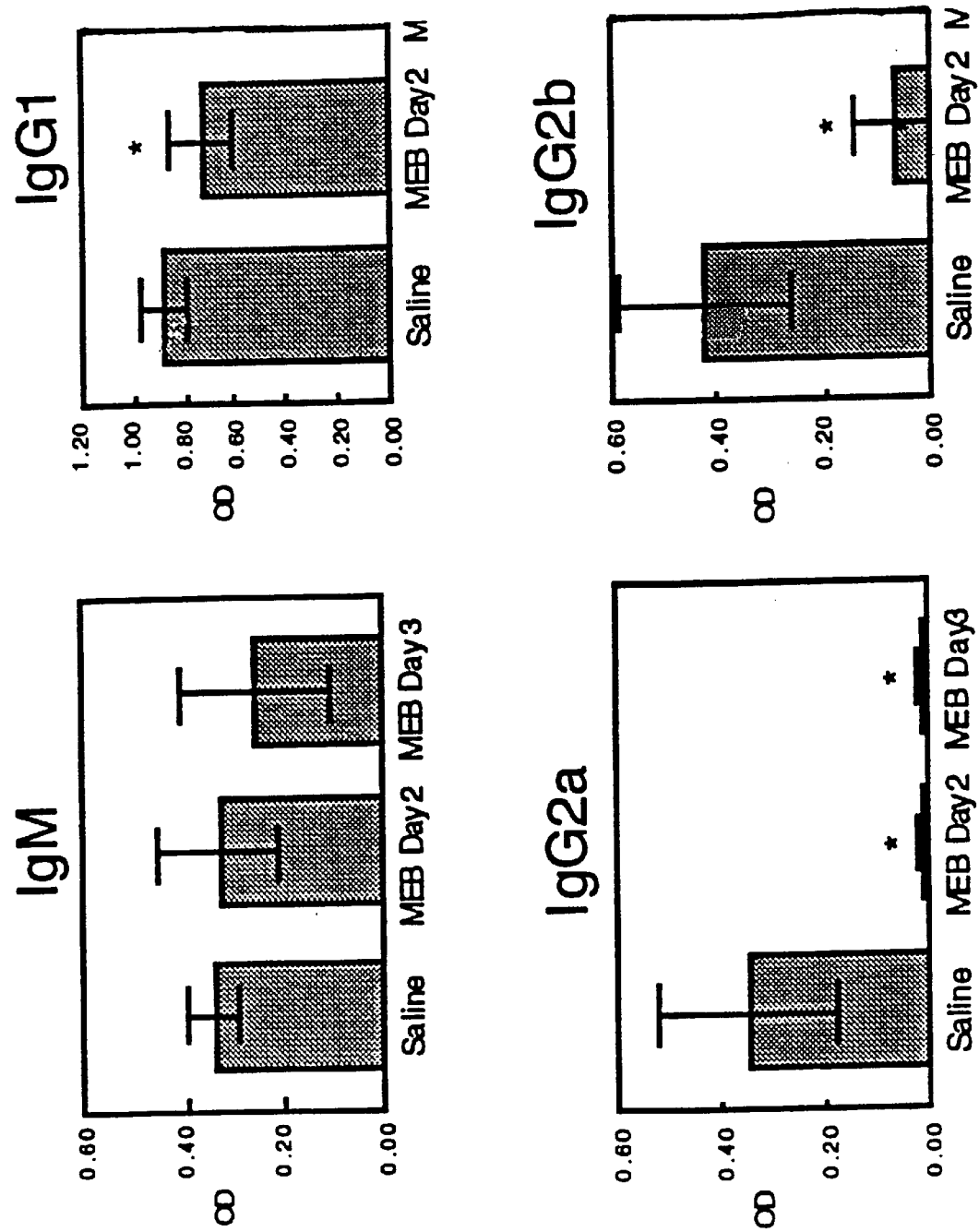
Figure 4C:
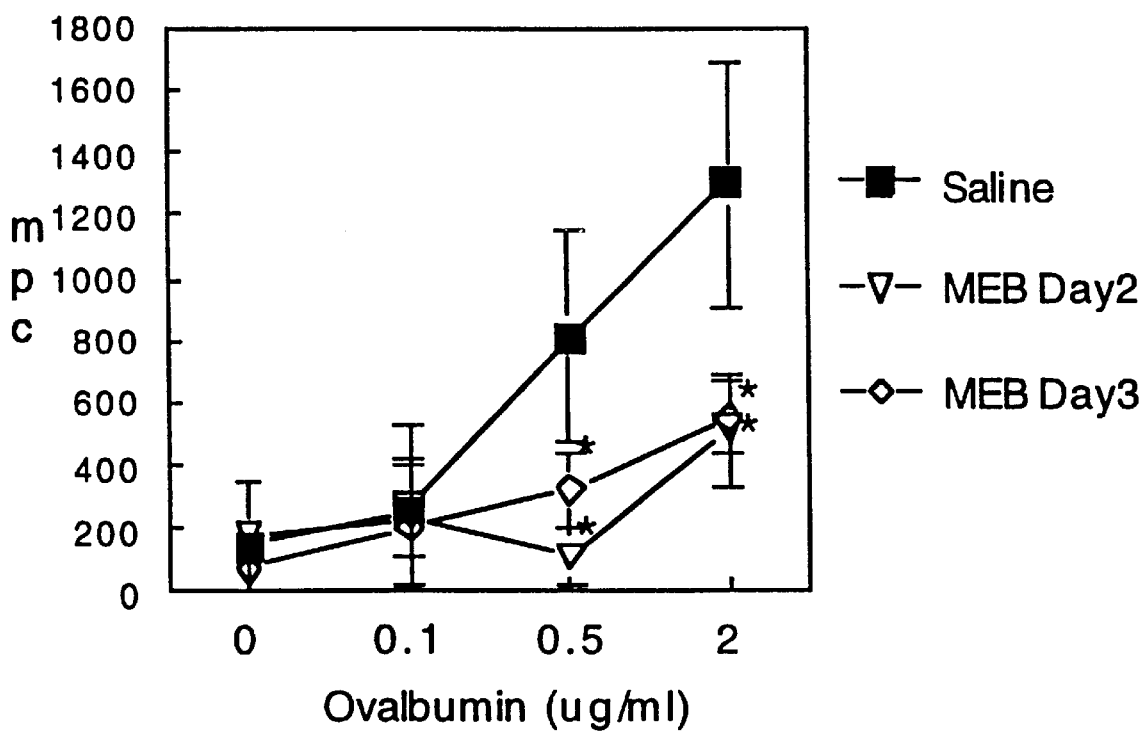

An evaluation of the antibody response generated by a second exposure to ovalbumin reveales that $IgG_{2a}$ and $IgG_{2b}$, anti-ovalbumin antibody remain dramatically low (decreased by at 80% compared to controls) in mice treated with MEB on either day 2 or day 3 following their initial immunization with ovalbumin (FIG. 4B). IgG1 anti-ovalbumin production during the secondary antibody response is also significantly decreased, while the IgM anti-ovalbumin antibody production following reimmunization with ovalbumin is unaffected by the initial treatment with MEB. The MEB-induced decrease in IgG antigen-specific antibody production correlates with a significant loss of antigen-specific proliferation observed in the CD4$^+$T cells isolated from antigen-primed mice treated with MEB on day 2 or day 3 following immunization (FIG. 4C). Taken together even a brief exposure to the butyrate derivative MEB in vivo can induce antigen-specific unresponsiveness in CD4$^+$T cells.

EXAMPLE 10

Butyrate derivative induced antigen-specific inactivation in CD4$^+$T cells in vitro To demonstrate the ability of MEB to induce antigen-specific unresponsiveness in CD4$^+$T cells in vitro, it is necessary to determine whether antigen is required for MEB-induced T cell anergy. Th1 cells are treated with MEB in the presence or absence of antigen or exogenous IL-2. The Th1 cells are then removed from the primary cultures, washed free of MEB, and re-stimulated with antigen or IL-2 in secondary cultures; tolerized Th1 cells are characterized by the fact that although they lose their ability to proliferate when restimulated with antigen, their continued expression of IL-2 receptors enables them to proliferate when stimulated with exogenous IL-2.

FIG. 2 shows that Th1 cells treated with IL-2 and MEB, although blocked in primary cultures, retain their ability to proliferate in response to IL-2 once the MEB has been washed from the cultures. Th1 cells pretreated with IL-2 and MEB also retain their ability to proliferate to antigen once MEB has been washed from the cultures (FIG. 5A). In contrast to Th1 cells pretreated with IL-2 and MEB, Th1 cells pretreated with antigen and MEB lose their ability to proliferate in antigen-stimulated secondary cultures (FIG. 5B). The fact that the Th1 cells pretreated with antigen and MEB, although unable to respond to antigen, can still proliferate in secondary cultures stimulated with exogenous IL-2, suggests that the lack of antigen responsiveness in these Th1 cells is not due to a loss of viability. Th1 cells incubated in primary cultures with MEB alone, or in medium alone retain their ability to proliferate in response to antigen stimulation in secondary cultures. This result shows that antigen-activated, but not IL-2-activated, Th1 cells become unresponsive to a subsequent stimulation with antigen following exposure to MEB.

EXAMPLE 11

MEB induction of alloantigen-specific T cell unresponsiveness

The ability of MEB to induce alloantigen-specific T cell unresponsiveness is shown by incubating spleen cells from DBA/2 mice (H-2$^d$) (2.5×10$^5$ in 200 µl/wells) with stimulator cells [2.5×10$^5$ irradiated (2000R) spleen cells from C57BL/10 mice (H-2$^b$)]. MEB (1 mM) is added to some wells of the mixed lymphocyte reaction (MLR) 24 hours after the initiation of culture. After an additional 3 days, the MLR cultures are washed, and rested for a further 2 days. The T cells from the MLR are then isolated and reincubated at 2.5×10$^5$ /well with either the initial alloantigen (spleen cells from C57BL/10 mice), or with a third-party alloantigen [spleen cells from C3H/HeJ mice (H-2$^k$)]. Proliferation in both the primary and secondary MLR is measured on day 5 by assessing incorporation of [$^3$H]-TdR after a 12 hour pulse.

Figure 6A:
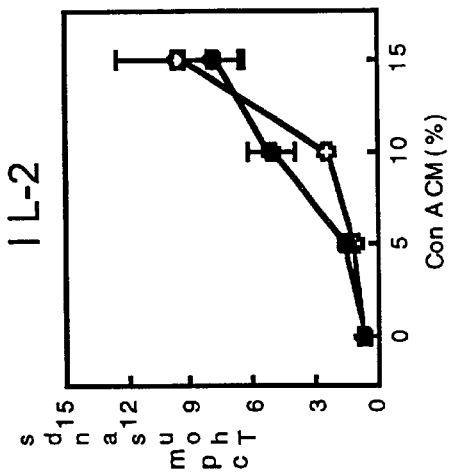
(FIG. 6A) Spleen cells from DBA/2 mice ($H-2^d$) were stimulated in a primary mixed lymphocyte response (MLR) with irradiated spleen cells or from C57BL/10 mice ($H-2^b$) in the presence (○) or absence (●) of MEB (1 mM). As a negative control some wells are stimulated with spleen cells from DBA/2 mice (▼). Proliferation is measured on day 5.
Figure 6A:
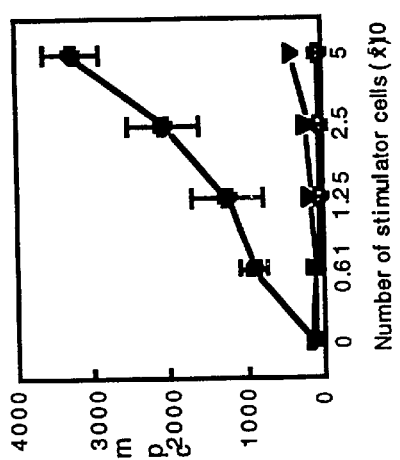
Figure 6B:
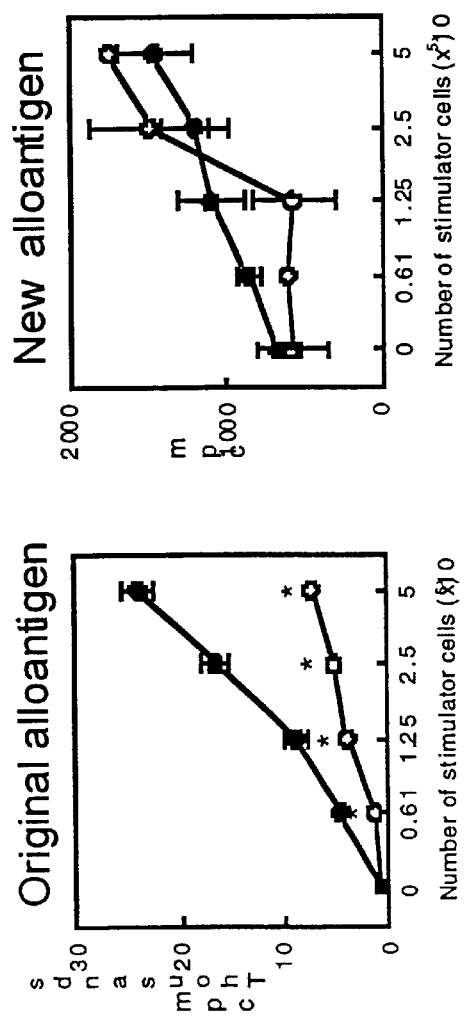
(FIG. 6B) After 3 days, some wells in the primary MLR cultures are washed, and rested for a further 2 days. The spleen cells that were stimulated in the primary MLR with spleen cells from C57BL/10 mice in the presence (○) or absence (●) of MEB are then isolated and reincubated with either the original alloantigen (spleen cells from C57BL/10 mice), with a third-party alloantigen [spleen cells from C3H/HeJ mice ($H-2^k$)], or with IL-2 (Con A CM). Proliferation was measured on day 5 of the secondary MLR. *Significantly different from response of spleen cells not exposed in the primary MLR to MEB, p<0.01.

MEB addition blocked spleen cell proliferation in a primary one-way MLR (FIG. 6A). More interestingly, splenic T cells incubated with MEB during the primary MLR lose their ability to proliferate when restimulated with the initial alloantigen in a secondary MLR that does not contain MEB. However, the T cells treated with MEB in the presence of the initial alloantigen are able to proliferate when restimulated with a third-party alloantigen or exogenous IL-2. In contrast to the T cells isolated from the MEB-treated MLR, T cells isolated from a primary MLR that does not contain MEB, are able to proliferate when restimulated with the initial alloantigen or with a third-party alloantigen. Thus, MEB-induced unresponsiveness is not generalized, but occurs only in those T cells which are simultaneously stimulated with antigen.

EXAMPLE 12

Butyrate derivative blocked activated Th1 cells in $G_1$

The ability of the butyrate derivative to induce Th1 cell anergy is examined using a protocol previously developed for n-butyrate-induced T cell tolerance (Gilbert and Weigle, 1993). Briefly, Th1 cells are incubated in primary cultures at 2.5×10$^5$ cells/ml, along with MEB (1 mM), KLH (50 µg/ml), and 5×10$^6$ /ml irradiated syngeneic spleen cells as APC. Alternatively, the Th1 cells are incubated in primary cultures containing MEB and IL-2 (10% Con A CM). Control primary cultures receive MEB and APC, but no antigen or IL-2. After incubation for 24 h at 37° C., the cells in the primary cultures are harvested, washed free of MEB, and reincubated at 2.5×10$^5$ml in secondary cultures without MEB. The Th1 cells in the secondary cultures are stimulated with 10% IL-2-containing Con A CM, or with 5×10$^6$/ml irradiated syngeneic spleen cells as APC, and KLH. After 2 days in the secondary cultures, the Th1 cells are assessed for proliferation (pulsed with [$^3$H]-TdR for 12 h).

Figure 7:
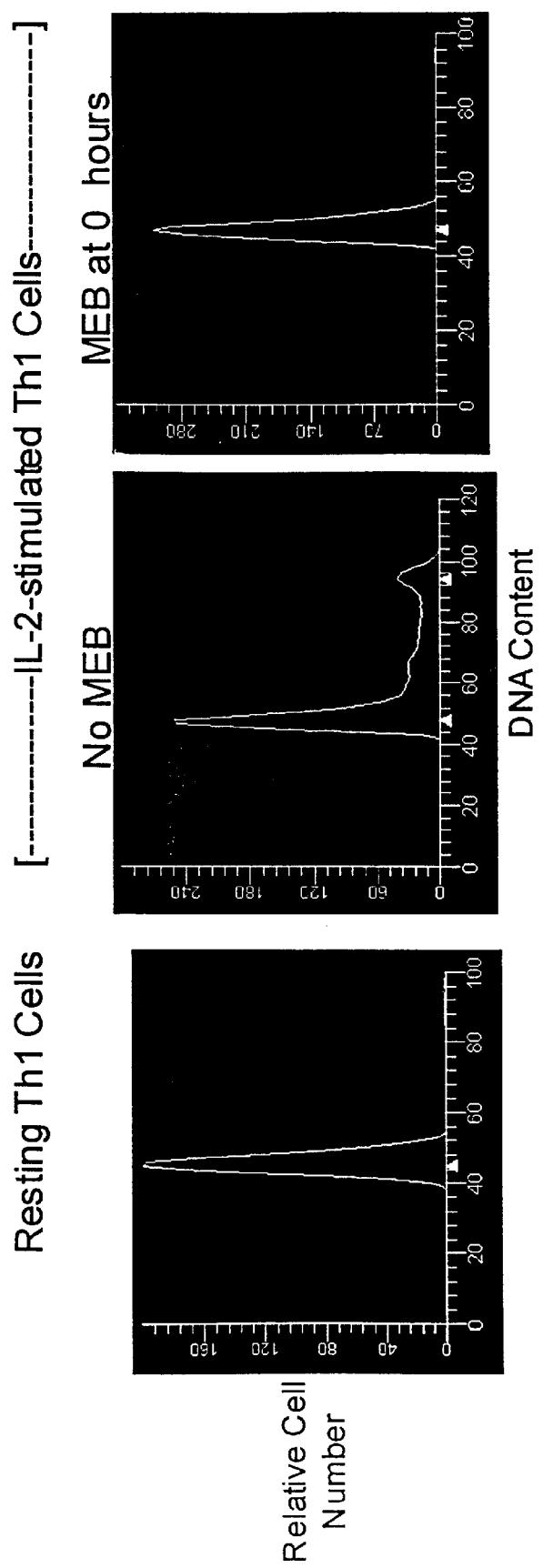
FIG. 7 shows that MEB blocks Th1 cell cycle progression in $G_0/G_1$. KLH-specific Th1 cells (clone C3) are left unstimulated (resting), or are stimulated with IL-2 (10% Con A CM) in the presence or absence of MEB (1 mM). The Th1 cells are collected after 48 hours, and assayed for DNA content.
Figure 8A:
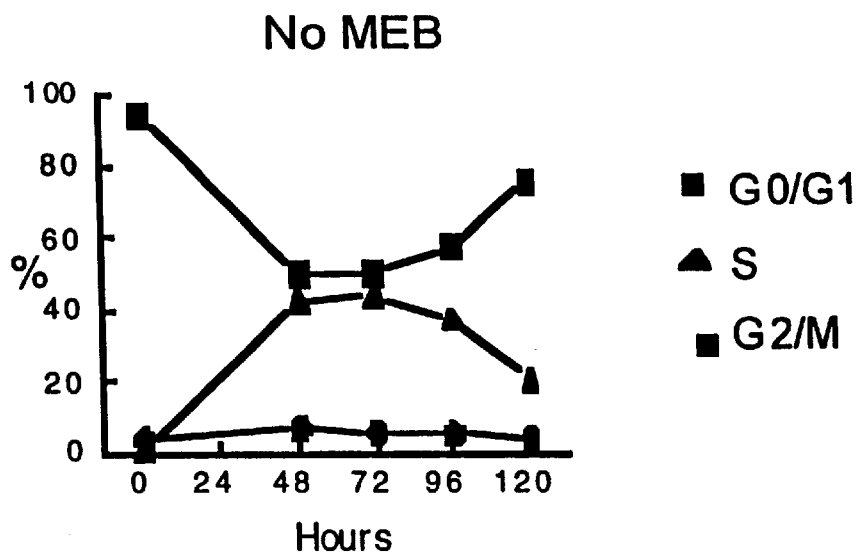
FIG. 8 shows that MEB sequesters stimulated Th1 cells in $G_0/G_1$. KLH-specific Th1 cells (clone C3) were stimulated with IL-2 (10% Con A CM) at the initiation of culture, and then again at 24, 48, and 96 hours (FIG. 8A). Some cultures also received a single dose of MEB (1 mM) at times 0, 15, 24 or 39 hours after the initiation of culture (FIGS. 8B, 8C, 8D, and 8E, respectively). The Th1 cells were collected at 0, 48, 72, 96 or 120 hours after the initiation of culture and assayed for DNA content.
Figures 8B, 8C:
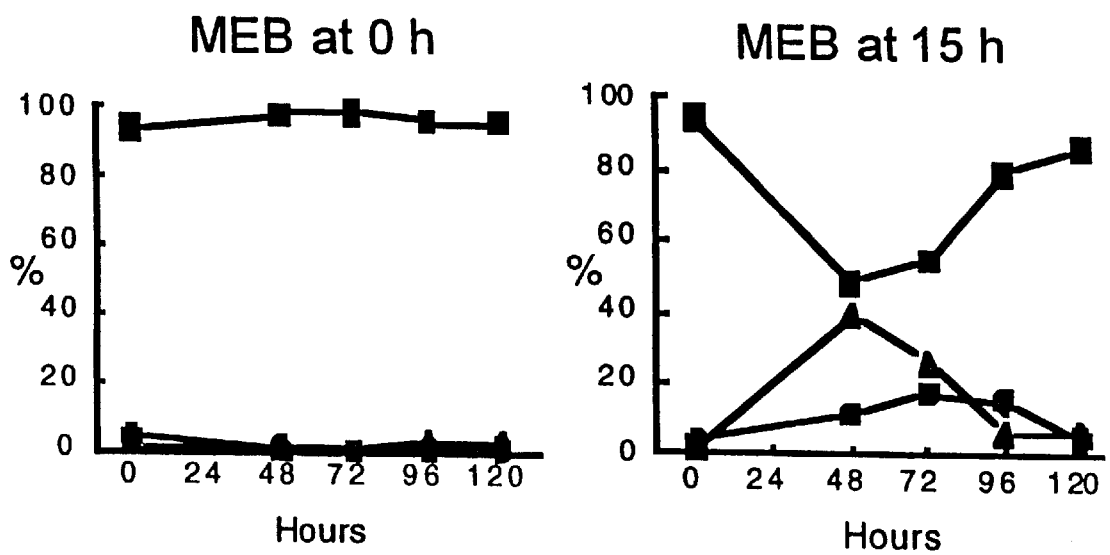
Figure 8D:
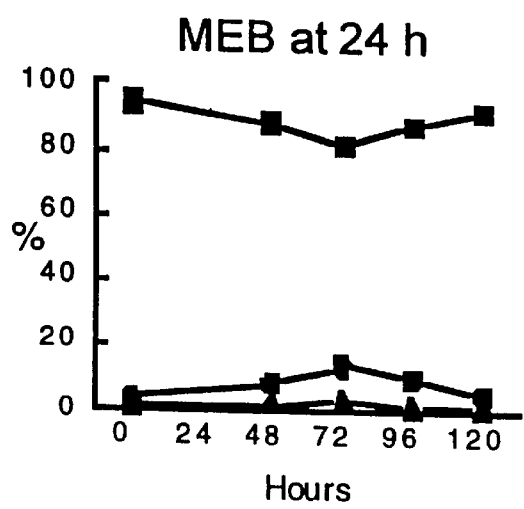
Figure 8E:
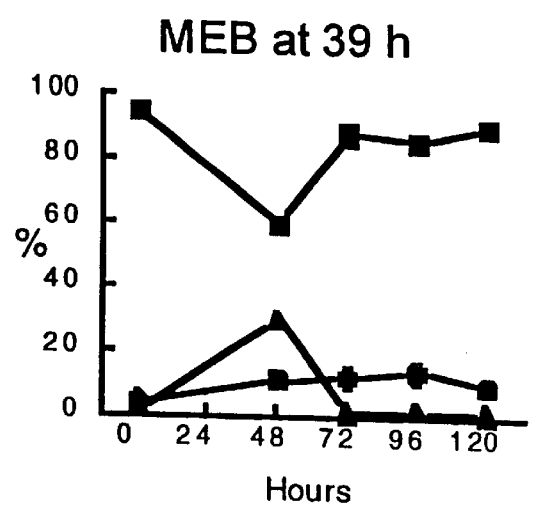

Since MEB appeared to suppress antigen-specific T cell responses both in vivo and in vitro, further characterization of its mechanism of action was conducted. n-Butyrate-induced T cell tolerance has been linked to the ability of the compound to block cell cycle progression of T cells in G. (Gilbert and Weigle, 1993). Although it was shown that MEB, as well as other butyrate derivatives, inhibited the proliferation of activated Th1 cells, it was not known where in the cell cycle this inhibition occurred. An analysis of DNA content showed that similar to n-butyrate, essentially all the Th1 cells stimulated with IL-2 in the presence of MEB remained in $G_0/G_1$ (FIG. 7).

EXAMPLE 13

Butyrate derivative sequestered activated Th1 cells in $G_0G_1$

If the ability of butyrate and its derivatives to induce Th1 cell tolerance is linked to their ability to block antigen-activated Th1 cells in $G_1$, their therapeutic importance is enhanced if MEB induces $G_1$ cell cycle blockade regardless of when in the cell cycle the compound is added. MEB is added to cultures of IL-2-stimulated Th1 at various time points. In the absence of MEB, it is shown that approximately 50% of IL-2-activated Th1 cells have exited $G_1$ by Day 2 (FIG. 8). In contrast, if MEB is added at the initiation of culture, over 97% of the IL-2-stimulated Th1 cells remain in $G_0/G_1$ for the duration of the experiment (120 hours). If MEB is not added until 15 hours after the Th1 cells are stimulated with IL-2, the initial cell cycle progression is similar to that seen in the absence of inhibitor, but by 96 hours, 79.3% of the IL-2-stimulated Th1 cells are blocked in $G_0/G_1$, compared to only 56.9% in control cultures. If MEB is added 24 hours instead of 15 hours after IL-2 stimulation, 89% of the Th1 cells are blocked in $G_1$ phase by 48h, and the cell cycle profile looks very similar to that obtained if MEB is added at the initiation of culture. Finally, even if MEB is added as late as 39 hours after IL-2 stimulation, 87% of the Th1 cells (as compared to 49.9% of controls) are sequestered in $G_0/G_1$, when DNA content is measured at 72 hours. Very similar cell cycle kinetics are obtained when n-butyrate instead of MEB is added to cultures of IL-2-stimulated Th1 cells (data not shown).

Taken together, this data suggests that if activated Th1 cells are exposed to MEB when the Th1 cells are still in $G_0/G_1$, MEB-induced cell cycle blockade is immediate and dramatic. Similarly, if MEB is added at 24 hours, the time at which the majority of Th1 cells have apparently completed one cell cycle and are back in $G_1$, an immediate and effective cell cycle blockade is again observed. If MEB is added at a time (e.g. 15 or 39 hours after stimulation) when at least some of the activated Th1 have already exited $G_1$, the Th1 cells have to cycle back to $G_1$ in order to become susceptible to MEB-induced cell cycle blockade, but eventually essentially all the activated Th1 cells are blocked in $G_1$ by MEB.

Therefore, MEB induces eventual $G_1$ sequestration of activated Th1 cells no matter when it is added during the cell cycle. This suggests that MEB will be effective in treating an ongoing T cell response, a valuable characteristic of an immunotherapeutic agent. Many methods of inducing antigen-specific T cell unresponsiveness for the treatment of autoimmunity are very useful in preventing the initiation of the disease process, but are much less effective in treating an already established autoimmune response (Bai et al., 1998; Meyer et al., 1996; Gaupp et al., 1997). In addition, use of butyrate derivatives to treat autoimmune disease does not require identification of the specific autoantigens targeted by the self-reactive lymphocytes. Theoretically, the butyrate derivatives would inactivate any $CD4^+T$ cell that was simultaneously being stimulated with antigen, thus encompassing all autoreactive $CD4^+T$ cells activated in response to any self-antigens.

Thus, the short-term use of butyrate derivatives can be used in vivo to induce antigen-specific inactivation of at least the Th1 cell-like subset of $CD4^+T$ cells, thereby providing the basis for a novel method of immune intervention with potential for the treatment of autoimmune disease. Such a treatment regimen has definite advantages over most existing immunotherapies which consist of long-term use of drugs that induce generalized immune suppression and may produce significant clinical side effects.

EXAMPLE 14
DNA analysis

To examine DNA content, Th1 cells were fixed in prechilled 70% ethanol overnight at 4° C. The fixed Th1 cells were next washed in PBS, resuspended in 1 ml of staining buffer containing RNase (1 mg/ml; Sigma) and propidium iodide (50 µg/ml; Sigma), incubated for 20 minutes in the dark at 20° C., and analyzed by flow cytometry using a FACSCalibur (Becton Dickinson, Moutain View, Calif.). The data were analyzed using the ModFit DNA analysis program (Verity Software House).

EXAMPLE 15
In vivo administration of butyrate prodrugs

Effective suppression in vivo of $CD4^+T$ cells and the corresponding T cell-induced antibody response is dependent on when the prodrugs are administered. Butyrate has a half-life of six minutes; the butyrate prodrugs of the present invention possess a half-life in the range of several hours. No toxicity is observed in the present study when mice were treated with MEB at a dose which approximated 0.7 g/kg/day. Even if administered at high doses for extended periods of time it seems unlikely that MEB would be toxic. Concerns about possible sodium overload and lack of efficacy have precluded studies examining the potential toxicity of high doses of n-butyrate. However, the arginine salt of butyrate was shown to be nontoxic in humans even when perfused at doses as high as 2 g/kg/day (Perrine et al., 1994). The efficacy of a single dose of MEB suggests that short-term use of the compound would be effective, thus eliminating any possible toxicity associated with long term use.

MEB is able to inactivate $CD4^+T$ cells in vivo even if administered in a single dose. If MEB works in vivo as it does in vitro, i.e. by inducing anergy in antigen-stimulated T cells, it would be necessary for MEB to be present only during the narrow window of time when T cell stimulation by antigen occurs in vivo. Since T cell activation in draining lymph nodes has been shown to occur 2–3 days following immunization of naive mice (Garside et al., 1998; MacLennan et al., 1997), MEB was administered in a single dose on either day 2 or day 3 following administration of the antigen, in this case ovalbumin. Both primary and secondary anti-ovalbumin antibody production is inhibited in the MEB-treated mice. However, not all the isotypes of anti-ovalbumin antibody are suppressed equally. IgM anti-ovalbumin is slightly inhibited during the primary antibody response, and is totally unaffected during the secondary antibody response. Since, the requirement for antigen-specific T cell help during the production of IgM is less stringent than that needed for the production of IgG subclasses of Ig (Steele et al., 1996), this finding would suggest that MEB is better at suppressing specific T cell responses than it is at inhibiting non-specific T cell help or B cell activity.

EXAMPLE 16
Effect of MEB treatment on antigen-specific antibody production

Although a single dose of MEB has little effect on antigen-specific IgM production, this treatment regimen suppresses primary $IgG_{2a}$ and $IgG_{2b}$ anti-ovalbumin antibody production, and blocks the generation of the memory T cells required for a secondary $IgG_{2a}$ or $IgG_{2b}$ anti-ovalbumin antibody response. MEB also decreases the generation of memory T cells required for a secondary $IgG_1$ antibody response. However, the effect of MEB treatment on $IgG_1$ antibody production is less profound than the effect of MEB on $IgG_{2a}$ or $IgG_{2b}$. $IgG_1$ production is dependent on IL-4, and thus largely driven by Th2 cells, while $IgG_{2a}$ production is enhanced by IFN-$\gamma$, and thus driven by Th1 cells (Stevens et al., 1988). The relationship between $IgG_{2b}$ and a particular $CD4^+T$ cell subset is less well-defined, but since IL-4 suppresses $IgG_{2b}$ (Kuhn et al., 1991), it is not unlikely that Th1 cells rather than Th2 cells promote $IgG_{2b}$ production in vivo. Consequently, it is possible to interpret the differential effect of MEB on isotype-specific antibody production in vivo by postulating that Th1 cells are more susceptible than Th2 cells to MEB-induced unresponsiveness. The results showing that MEB induced antigen-specific unresponsiveness in Th1 cells in vitro underscore the likelihood that Th1 cells, both in vitro and in vivo, are susceptible to MEB-induced tolerance. The suggestion that Th2 cells are less susceptible than Th1 cells to MEB-induced unresponsiveness is in accordance with other methods of inducing T cell tolerance which have similarly documented the relative resistance of Th2 cells to tolerance induction (Gilbert et al., 1990; Williams et al., 1990). The fact that the memory $IgG_1$ antibody response is suppressed to some degree in mice treated with MEB suggests that although Th2 cells may be somewhat resistant to MEB-induced unresponsiveness, somewhat longer exposure to MEB, or perhaps higher doses of MEB may be expected to more completely suppress Th2-mediated $IgG_1$ production.

MEB-induced T cell unresponsiveness was not generalized, but was reserved for T cells that were simultaneously stimulated with antigen. Unlike Th1 cells exposed to both antigen and MEB in vitro, Th1 cells exposed to MEB alone, or to MEB and IL-2, did not lose their ability to respond to a subsequent antigen challenge. Along these same lines, splenic T cells stimulated in vitro with an alloantigen in the presence of MEB lost their ability to proliferate in response to a subsequent challenge with the initial alloantigen, but retained their ability to proliferate when stimulated with a third-party alloantigen. Taken together, these results underscore the antigen specificity of MEB-induced T cell unresponsiveness.

The following references are cited herein:

Bai X F, Li H L, Shi F D, Liu J Q, Xiao B G, van der Meide P H and Link H (1998) Complexities of applying nasal tolerance induction as a therapy for ongoing relapsing experimental autoimmune encephalomyelitis (EAE) in DA rats. Clin Exp *Immunol* 111: 205–210.

Daniel P, Brazier M, Cerutti I, Pieri F, Tarvidel I, Desmet G, Baillet J and Chany C (1989) Pharmacokinetic study of butyric acid administered in vivo as sodium and arginine butyrate salts. *Clin.Chim.Acta* 181: 255–264.

Garside P, Ingulli E, Merica R R, Johnson J G, Noelle R J and Jenkins M K (1998) Visualization of specific B and T lymphocyte interactions in the lymph node. *Science* 281: 96–99.

Gaupp S, Hartung H P, Toyka K and Jung S (1997) Modulation of experimental autoimmune neuritis in Lewis rats by oral application of myelin antigens. *J Neuroimmunol* 79: 129–137.

Gilbert K M, Hoang K D and Weigle W O (1990) Th1 and Th2 clones differ in their response to a tolerogenic signal. *J.Immunol.* 144: 2063–2071.

Gilbert K M and Weigle WO (1993) Th1 cell anergy and blockade in Gla phase of the cell cycle. *J.Immunol.* 151: 1245–1254.

Griffin J M, Blossom S J, Jackson S K, Gilbert K M and Pumford N R (2000) Trichloroethylene accelerates an autoimmune response in association with Th1 T cell activation in MRL +/+ mice. Submitted.

Kruh J, Defer N and Tichonicky L (1992) Molecular and cellular action of butyrate. *C.R.Seances Soc.Biol.Fil.* 186: 12–25.

Kuhn R, Rajewsky K and Muller W (1991) Generation and analysis of Interleukin-4-deficient mice. *Science* 254: 707.

MacLennan I C M, Gulranson-Judge A, Toellner K, Casamayor-Palleja M, Chan E, Sze D M, Luthre S A and Orbea H A (1997) The changing preference of T and B cells for partners as T-dependent antibody responses develop. *Immunol.Rev.* 156: 54–66.

Meyer A L, Benson J M, Gienapp I E, Cox K L and Whitacre C C (1996) Suppression of murine chronic relapsing experimental autoimmune encephalomyelitis by the oral administration of myelin basic protein. *J Immunol* 157: 4230–4238.

Miller A A, Kurschel E, Osieka R and Schmidt C G (1987) Clinical pharmacology os sodium butyrate in patients with acute leukemia. *Eur.J.Cancer Clin.Oncol.* 23: 1283–1287.

Novogrodsky jA, Dvir A, Ravid A, Shkolnik T, Stenzel K H, Rubin A L and Zaizov R (1983) Effect of polar organic compounds on leukemic cells. Butyrate-induced partial remission of acute myelogenous leukemia in a child. *Cancer* 51: 9–14.

Perrine S P, Olivieri N F, Faller D V, Vichinsky E P, Dover G J and Ginder G D (1994) Butyrate derivatives. New agents for stimulating fetal globin production in the P-globin disorders. *Am.J.Pediatr.Hematol.Oncol.* 16: 67–71.

Steele D J, Laufer T M, Smiley S T, Ando Y, Grusby M J, Glimcher L H and Auchincloss H J (1996) Two levels of help for B cell alloantibody production. *J Exp Med* 183: 699–703.

Stevens T L, Bossie A, Sanders V M, Fernandez-Botran R, Coffman R L, Mosmann T R and Vitetta E S (1988) Regulation of antibody isotype secretion by subsets of antigen-specific helper T cells. *Nature* 334: 255–258.

Williams M E, Lichtman A H and Abbas A K (1990) Anti-CD3 antibody induces unresponsiveness to IL-2 in Th1 clones but not in Th2 clones. *J.Immunol.* 144: 1208–1214.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. The compound of the structure

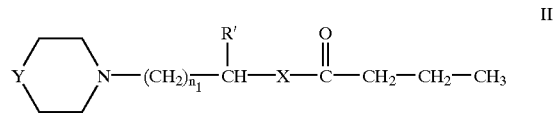

wherein $n_1$ is 1–5;

X is NH;

Y is O.

2. A pharmaceutical composition, comprising a compound of claim 1 and a pharmaceutically acceptable carrier or diluent.

* * * * *

UNITED STATES PATENT AND TRADEMARK OFFICE
CERTIFICATE OF CORRECTION

PATENT NO. : 6,407,107 B1
DATED : June 18, 2002
INVENTOR(S) : Kathleen Gilbert and E. Kim Fifer It is certified that error appears in the above-identified patent and that said Letters Patent is hereby corrected as shown below:

<u>Column 18,</u>
Line 52, please insert -- R' is selected form the group consisting of methyl and ethyl; or a pharmaceutically acceptable salt thereof. --

Signed and Sealed this

Fifteenth Day of February, 2005

JON W. DUDAS
*Director of the United States Patent and Trademark Office*